US012635890B2

(12) United States Patent
Batzer

(10) Patent No.: US 12,635,890 B2
(45) Date of Patent: May 26, 2026

(54) MEDICAL IMAGING WITH ECG TRIGGERING

(71) Applicant: Siemens Healthcare GmbH, Erlangen (DE)

(72) Inventor: Ulrich Batzer, Spardorf (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 1226 days.

(21) Appl. No.: 17/400,324

(22) Filed: Aug. 12, 2021

(65) Prior Publication Data

US 2022/0054021 A1      Feb. 24, 2022

(30) Foreign Application Priority Data

Aug. 18, 2020      (DE) ..................... 10 2020 210 455.7

(51) Int. Cl.
*A61B 5/0205*      (2006.01)
*A61B 5/00*      (2006.01)

(52) U.S. Cl.
CPC .......... *A61B 5/0205* (2013.01); *A61B 5/7289* (2013.01)

(58) Field of Classification Search
CPC .................................................... A61B 5/0205
See application file for complete search history.

(56) References Cited

U.S. PATENT DOCUMENTS

| | | | |
|---|---|---|---|
| 8,519,706 | B2 | 8/2013 | Landschuetz et al. |
| 2003/0114749 | A1 | 6/2003 | Rahn |

| | | | | |
|---|---|---|---|---|
| 2006/0287594 | A1 | 12/2006 | Boese et al. | |
| 2008/0123812 | A1 | 5/2008 | Sabol et al. | |
| 2008/0154121 | A1 | 6/2008 | Kouwenhoven | |
| 2010/0217139 | A1 | 8/2010 | Pinter et al. | |
| 2011/0152669 | A1 | 6/2011 | Kassai | |
| 2012/0307964 | A1 | 12/2012 | Hall et al. | |
| 2015/0238149 | A1* | 8/2015 | Nitta ................... | A61B 5/0044 600/413 |
| 2016/0074674 | A1* | 3/2016 | Kohli .................. | A61B 5/0531 600/484 |
| 2016/0287203 | A1 | 10/2016 | Koike et al. | |
| 2019/0374189 | A1 | 12/2019 | Kiely | |
| 2022/0386987 | A1* | 12/2022 | Camps ................ | A61B 5/0205 |

FOREIGN PATENT DOCUMENTS

| | | |
|---|---|---|
| DE | 102005027944 A1 | 1/2007 |
| DE | 102009061198 B3 | 2/2014 |
| DE | 102016205088 A1 | 10/2016 |
| WO | WO 2019140155 A1 | 7/2019 |

OTHER PUBLICATIONS

German Office Action dated Jun. 25, 2021.

* cited by examiner

*Primary Examiner* — Patricia J Park
(74) *Attorney, Agent, or Firm* — Harness, Dickey & Pierce, P.L.C.

(57)      ABSTRACT

A method is for medical imaging of a patient using a medical imaging system with ECG triggering. In an embodiment, the method includes capturing a respiration signal of the patient including n respiration cycles; concurrently capturing an ECG signal of the patient including m heartbeat intervals; determining a respiration-dependent heartbeat model based upon the n respiration cycles and the m heartbeat intervals; specifying at least one trigger time-point based upon the respiration-dependent heartbeat model; and starting the medical imaging at the specified trigger time-point.

17 Claims, 4 Drawing Sheets

MEDICAL IMAGING WITH ECG TRIGGERING

PRIORITY STATEMENT

The present application hereby claims priority under 35 U.S.C. § 119 to German patent application number DE 102020210455.7 filed Aug. 18, 2020, the entire contents of which are hereby incorporated herein by reference.

FIELD

Example embodiments of the invention generally relate to a device/method for medical imaging with ECG triggering, wherein trigger time-points are specified taking the respiration of a patient into consideration.

BACKGROUND

If the heart requires a medical imaging examination, the cardiac movement, which may amount to several centimeters in a few hundred milliseconds and can therefore significantly impair the imaging quality, must be taken into consideration.

In order to minimize interference effects of the cardiac movement, an image data capture can take place iteratively at a specific cardiac phase in each case, where it is assumed that the heart is in the same state of movement and therefore in the same position. The time-points of the heartbeats must be captured for this purpose, e.g. via ECG or a pulse wave signal of a patient. It is then endeavored based upon the previous heartbeats to draw conclusions in respect of the following heartbeats in order to trigger the image data capture. The temporal irregularity of the heartbeats presents a problem. The time between two heartbeats can double or halve from one heartbeat to the next, and therefore predictions relating to imminent cardiac phases can be incorrect.

The German patent application DE 102005027944 A1 proposes a method which attempts to take the irregularities in the heartbeat into consideration based upon an ECG signal and, as a function of the irregularity, to estimate the trigger time-points for the subsequent heartbeats accordingly.

A significant cause of an irregular heartbeat is respiration. This respiration-dependent irregularity is also known as respiratory sinus arrhythmia. The respiratory sinus arrhythmia is manifested in an increased heart rate when inhaling and a decreased heart rate when exhaling. The effect of the respiration on the heart rate is slightly delayed in this case. During an inhalation phase, the heart rate of a patient is approximately 60-80 beats per minute. During an exhalation phase, the heart rate is typically e.g. 40-60 beats per minute or less. The duration of the isoelectrical cardiac phase of a heartbeat interval without electrical activity, and to a similar extent the phase without cardiac movement, which are particularly attractive for image data capture since they cause little interference, can even double in the exhalation phase.

SUMMARY

At least one embodiment of the present invention provides a way for improved image data capture to be achieved by determining a trigger time-point in a reliable and reproducible manner. In particular, at least one embodiment of the present invention improves the image data capture by taking the patient respiration into consideration when specifying a trigger time-point for the image data capture.

At least one embodiment of the invention is directed to a method for the medical imaging of a patient using a medical imaging system with ECG triggering, a corresponding computing unit and a corresponding system. Preferred and/or alternative advantageous embodiment variants are specified in the claims.

Method and apparatuses are described below. Features, advantages or alternative embodiment variants cited in this context also apply likewise to the other subject matter and vice versa. In other words, material claims (directed to e.g. a method) can also be developed by features that are described or claimed in connection with one of the apparatuses. The corresponding functional features of the method in this case are designed as corresponding material modules or units.

In a first embodiment, the present invention relates to a method for the medical imaging of a patient using a medical imaging system with ECG triggering. In an embodiment, the method includes capturing a respiration signal of the patient including n respiration cycles; concurrently capturing an ECG signal of the patient including m heartbeat intervals; determining a respiration-dependent heartbeat model based upon the n respiration cycles and the m heartbeat intervals; specifying at least one trigger time-point based upon the respiration-dependent heartbeat model; and starting the medical imaging at the specified trigger time-point.

In a further embodiment, the invention relates to a computing unit for the medical imaging of a patient via a medical imaging system with ECG triggering. In an embodiment, the computing unit is configured to execute at least one embodiment of the inventive method. In an embodiment, the computing unit is therefore designed to capture a respiration signal of the patient comprising n respiration cycles, and concurrently to capture an ECG signal of the patient comprising m heartbeat intervals, to specify a respiration-dependent heartbeat model based upon the n respiration cycles and the m heartbeat intervals, to specify at least one trigger time-point based upon the respiration-dependent heartbeat model, and to start medical imaging via a medical imaging system at the specified trigger time-point.

In a further embodiment, the invention relates to a system for the medical imaging of a patient via a medical imaging system with ECG triggering. The system comprises:

a capture unit which is designed to capture a respiration signal of the patient comprising n respiration cycles, and concurrently an ECG signal of the patient comprising m heartbeat intervals;

a computing unit which is designed to specify a respiration-dependent heartbeat model based upon the n respiration cycles and the m heartbeat intervals, and a trigger time-point based upon the respiration-dependent heartbeat model; and a medical imaging system which is designed to start medical imaging at the specified trigger time-point.

In a further embodiment, the invention relates to a method for the medical imaging of a patient using a medical imaging system with ECG triggering, the method comprising:

capturing a respiration signal of the patient, the respiration signal including n respiration cycles;

concurrently capturing an ECG signal of the patient, the ECG signal including m heartbeat intervals;

determining a respiration-dependent heartbeat model based upon the n respiration cycles and the m heartbeat intervals;

specifying at least one trigger time-point based upon the respiration-dependent heartbeat model; and starting the medical imaging at the trigger time-point specified.

In a further embodiment, the invention relates to a computing unit for medical imaging of a patient using a medical imaging system with ECG triggering, the computing unit being designed to capture a respiration signal of the patient, the respiration signal including n respiration cycles;

concurrently capture an ECG signal of the patient, the ECG signal including m heartbeat intervals;

determine a respiration-dependent heartbeat model based upon the n respiration cycles and the m heartbeat intervals;

specify at least one trigger time-point based upon the respiration-dependent heartbeat model; and start the medical imaging at the at least one trigger time-point specified.

In a further embodiment, the invention relates to a system for medical imaging of a patient via a medical imaging system with ECG triggering, comprising:

a capture unit designed to capture a respiration signal of the patient, the respiration signal including n respiration cycles, and concurrently capture an ECG signal of the patient, the ECG signal including m heartbeat intervals;

a computing unit designed to specify a respiration-dependent heartbeat model based upon the n respiration cycles and the m heartbeat intervals, and a trigger at least one trigger time-point based upon the respiration-dependent heartbeat model; and a medical imaging system designed to start the medical imaging at the at least one trigger time-point specified.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

In a further embodiment, a computing unit can interact with a computer-readable data medium, in particular in order to perform a method according to an embodiment the invention by way of a computer program including program code. Furthermore, the computer program can be retrievably stored on the machine-readable medium. In particular, the machine-readable medium can be a CD, DVD, Blu-Ray Disc, memory stick or hard disk. The memory 23, the specification unit 22 and the control unit 18 can be designed in the form of hardware or software.

For example, the specification unit 22 may be designed as a so-called FPGA (Field Programmable Gate Array) or comprise an arithmetic logic unit. In the example shown here, at least one computer program is stored in the memory 23 of the computing unit 12, wherein the computer program performs all method steps of an embodiment of the inventive method when the computer program is executed on the computer. The computer program comprises program code for executing the method steps of an embodiment of the inventive method.

Furthermore, the computer program can take the form of an executable file and/or be stored on a different computing system than the computing unit 12. For example, the x-ray image recording apparatus can be configured so that the computing unit 12 loads the computer program via an intranet or via the internet into its internal working memory in order to execute the method according to an embodiment of the invention.

In a further embodiment, the invention relates to a non-transitory computer readable medium storing computer code which, when run on at least one processor, configures the at least one processor to perform the method of an embodiment.

BRIEF DESCRIPTION OF THE DRAWINGS

The properties, features and advantages of this invention as described above and the manner in which these are achieved become clearer and easier to understand in the context of the following description of the example embodiments, these being explained in greater detail with reference to the drawings. This description does not imply that the invention is restricted to these example embodiments. Identical components are denoted by identical reference signs in the various figures. As a rule, the figures are not to scale.

DETAILED DESCRIPTION OF THE EXAMPLE EMBODIMENTS

Figure 1:
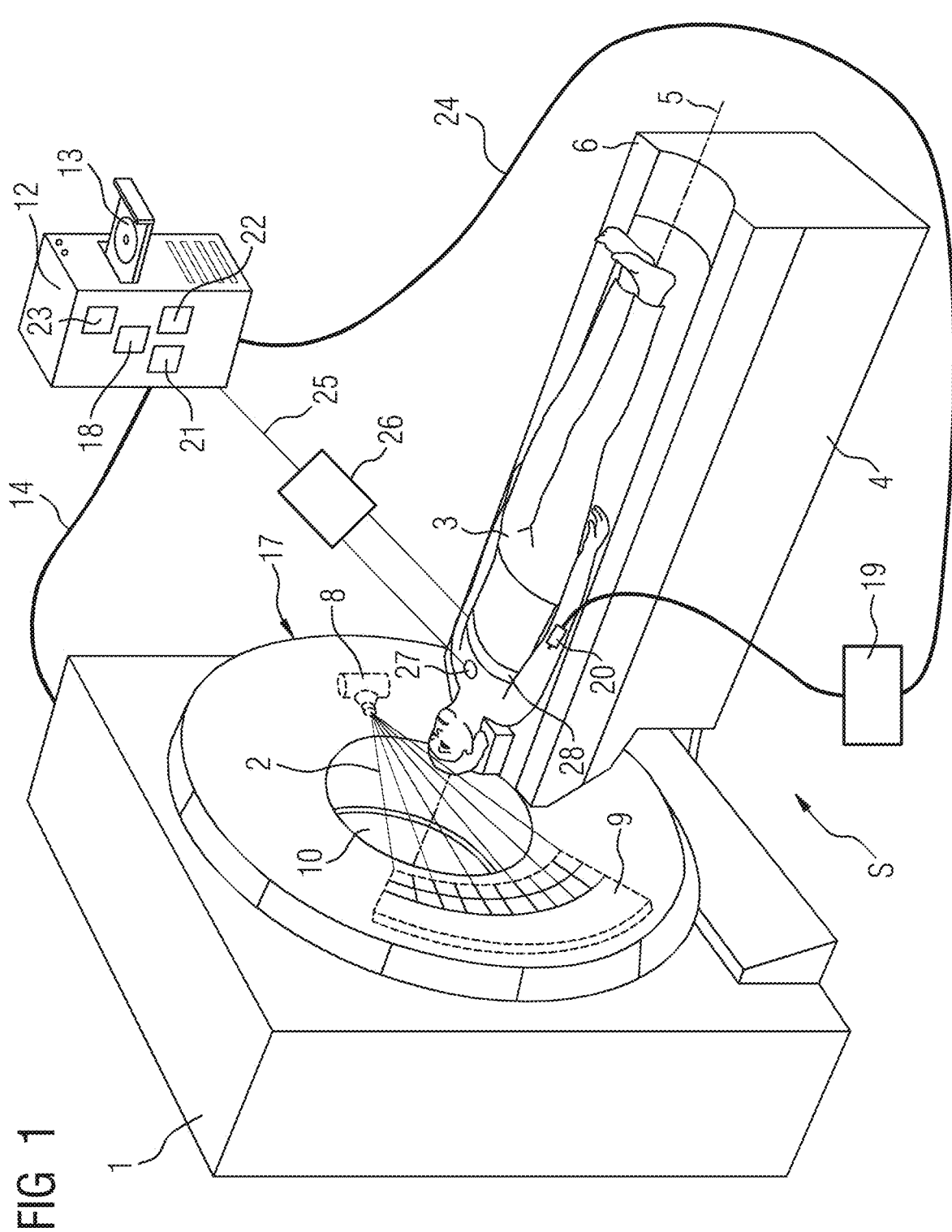
FIG. 1 shows a view of a system for medical imaging with ECG triggering, comprising a medical imaging system in the form of a computed tomography system according to an embodiment variant of the present invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In a first embodiment, the present invention relates to a method for the medical imaging of a patient using a medical imaging system with ECG triggering. The method comprises a plurality of steps.

In a first step, a respiration signal of the patient comprising n respiration cycles is captured. In a second step, an ECG signal of the patient comprising m heartbeat intervals is captured concurrently with the capture of the respiration signal. In a third step, a respiration-dependent heartbeat model is determined based upon the n respiration cycles and the m heartbeat intervals. In a fourth step, a trigger time-point is specified based upon the respiration-dependent heartbeat model. In a fifth step, the medical imaging is started at the specified trigger time-point.

The inventors have found that the specification of a suitable trigger time-point can be improved by taking the most frequent cause of irregular heartbeats, namely respiratory sinus arrhythmia (which is also present in healthy patients), into consideration using an additional measurement of a respiration signal, thereby allowing a more accurate prediction of the ongoing ECG signal. The invention is also based on the finding that the influence of the respiration is reflected in a temporal offset in the ECG signal and therefore the change in the heart rate can be predicted more effectively.

The capture of a respiration signal of the patient comprising n respiration cycles comprises measuring, detecting, monitoring and deriving a signal which represents the respiration of the patient. The respiration signal is captured over n (i.e. a plurality of) respiration cycles, at least over one respiration cycle and preferably over a plurality of respiration cycles, e.g. over 3, 5, 8, 10 or 20 respiration cycles. The captured respiration signal is formed in such a way that its profile allows a conclusion to be drawn in respect of patient respiration phases, in particular in respect of inhalation and exhalation phases.

The capture of the respiration signal can be effected in many different ways. The respiration signal can be provided via at least one expansion belt which is placed around the chest of the patient and measures a respiration-dependent expansion or change in length. The respiration signal can also be provided via a contactless radar sensor or a camera which captures in each case the movement or change in position of position markers that are attached to or arranged on the chest of the patient. Particularly advantageously, the capture of the respiration signal is effected by way of an impedance-based measurement via ECG electrodes which are placed on the patient and simultaneously serve to capture the ECG signal. The examination configuration is thereby reduced and the patient comfort is increased since only a few measuring apparatuses have to be attached.

The capture of an ECG signal of the patient comprising m heartbeat intervals comprises measuring, detecting, monitoring and/or deriving a signal which represents the heartbeat of the patient. The ECG signal is captured over m (i.e. a plurality of) heartbeat intervals, at least over the duration of a plurality of heartbeat intervals corresponding to the duration of a respiration cycle, e.g. over 8, 10, 12, 15, 16 or 20 heartbeat intervals. The captured ECG signal is formed in such a way that its profile allows a conclusion to be drawn in respect of cardiac phases of the patient. In particular, electrically active and isoelectrical phases within the heartbeat intervals can be specified.

The capture of the ECG signal can likewise be effected in many different ways. The capture of the ECG signal can comprise capturing the electrical potentials of the heart via ECG (electrocardiogram) electrodes or measuring the pulse wave via photoplethysmography or ballistocardiography. The capture of the ECG signal takes place concurrently, i.e. at the same time as the capture of the respiration signal.

The steps of capturing the respiration signal and the ECG signal and the determination of the heartbeat model can be temporally independent of the remaining method steps in each case. In other words, the capture of the respiration signal and the ECG signal and the determination of the respiration-dependent heartbeat model need not directly precede the remaining method steps. In a preferred embodiment, however, the method steps are performed in a temporally continuous sequence in order that the identification of trigger time-points can be based on a current heartbeat model.

In particular, if a respiration signal and ECG signal are captured by the same ECG electrodes, the synchronicity of the two signals is guaranteed. If the capture of the signals is effected by different measuring means, the synchronicity must be established or ensured via a clock generator, for example. This is particularly important because the relationship between respiration signal and ECG signal can vary for each patient and for each combination of measuring means in use. In this way, the influence of the respiration on the profile of the ECG signal can be determined as effectively as possible for each individual patient.

In principle, the respiration signal and the ECG signal can be captured from the moment at which one of the cited sensors is set up or activated. In particular, the respiration signal can also be captured over time intervals in which the patient was speaking, held their breath or moved. Provision can be made here for analyzing the respiration signal in respect of such irregularities and, when producing the heart-beat model, disregarding the respiration signal in identified time intervals. In other words, the heartbeat model is based on the assumption that the patient is at rest when the respiration signal is captured. Alternatively, time intervals in which the patient held their breath can be included in the heartbeat model on the assumption that, when the breath is held, the heart rate starting from the time-point at which the breath is held initially increases and then drops.

Without restricting general applicability, a patient assumes an examination object which is usually a human. In principle, the patient can also be an animal. The two terms "examination object" and "patient" are therefore used synonymously in the following.

A respiration-dependent heartbeat model is then determined from the captured respiration and ECG signals. In other words, this heartbeat model advantageously takes the respiration-related irregularities of the heartbeat into consideration by way of the respiration signal. The heartbeat model advantageously assigns heartbeat intervals to various respiration phases, in particular inhalation and exhalation phases. The heartbeat model also shows the respiration-related change in the duration of heartbeat intervals and/or cardiac phases.

The respiration-dependent heartbeat model is then used to specify or derive at least one trigger time-point. The method advantageously allows the simultaneous specification of multiple trigger time-points, in particular, multiple successive trigger time-points for a series of in particular successive heartbeat intervals. This is particularly advantageous for an image data capture which has to take place over an extended period of time. An image data capture is started at each of these multiple trigger time-points. Corresponding control signals for the imaging system are generated and transferred accordingly. The preferably multiple trigger time-points for a series of heartbeat intervals are inventively so established by the heartbeat model as to take the various respiration phases into consideration. As a result of defining the trigger time-points based upon the heartbeat model, it is ensured that multiple captures of image data all take place in the same cardiac phase or in the same cardiac state, whereby movement-related variations between the image data or indeed movement artifacts are minimized.

In a fifth step, the medical imaging is started at the at least one specified trigger time-point. In other words, a medical imaging system and/or further units involved in the image data capture are activated in this step by way of generated control signals in such a way that an image data capture starts at the trigger time-point.

With reference to at least one embodiment of the inventive heartbeat model, which is specific to an individual patient, it is therefore possible to make a precise heartbeat prediction or cardiac phase prediction for an imminent image data capture and to specify corresponding trigger time-points precisely. In particular, it is possible by way of the respiration-dependent heartbeat model to specify multiple trigger time-points within just one or within various heartbeat ranges (explained in greater detail below). Based upon this detailed and possibly long-term prediction in particular, the imaging system can, at a very early stage, start actions that are required for the imaging, e.g. moving a patient table or couch, preparing/adjusting imaging components, e.g. an x-ray source, or preparing and presetting a triggered contrast medium injection. In particular, heartbeat intervals and/or heartbeat ranges which are not intended for an image data capture and for which no trigger time-point has been specified can be used for such presettings. It is thereby possible to reduce the overall duration of the examination and advantageously to render the examination routine more effective.

Correspondingly, in a preferred embodiment of the inventive method, the starting of the medical imaging comprises a preconfiguration of the medical imaging system and/or further units in accordance with the respiration-dependent heartbeat model. This preconfiguration comprises, in addition to generating the actual start control signals at the control time-points that have been determined, generating further control signals which preconfigure the medical imaging system and/or further units such that these are adapted to the respiration-dependent heartbeat model. The preconfiguration can comprise the model-based generation of control signals for a patient couch, defining an initial position for the patient couch from which the image data capture is then started at the trigger time-point. The preconfiguration can additionally comprise the model-based generation of control signals for a contrast medium dosing unit, which specifies e.g. bolus sizes or contrast medium flow rates for individual heartbeat intervals or similar in accordance with the model. The preconfiguration can also comprise the model-based generation of control signals for e.g. the x-ray source of the imaging system, which can thus be adjusted to a required x-ray tube voltage at an early stage. The start control signals are then used to initiate the preset actions.

The imaging system therefore has, by virtue of the advance knowledge of imminent heartbeats and trigger time-points, an advantageously longer lead time for adaptations that are required. The occurrence of time periods for the image data capture having clock pulses that are too long or too short can be reduced thereby. The number of examinations with suboptimal outcomes can decrease.

As indicated above, in an embodiment of the inventive method, the determination of the respiration-dependent heartbeat model comprises dividing the respiration signal into at least two respiration phases. The two most important phases are the exhalation phase and the inhalation phase. Further respiration phases are possible, e.g. holding phases or resting phases. In other words, a respiration cycle is divided into at least two respiration phases, but can be structured more precisely with more than two phases. The division advantageously comprises the monitoring of the profile of the respiration signal, the identification of extreme points and/or reversal points within the respiration signal, and the assignment of the extrema and/or reversal points to respiration phase transitions. For example, an identified signal minimum can be assigned to a beginning of an inhalation phase and a signal maximum to a beginning of an exhalation phase. The division can also comprise specifying the duration of each respiration cycle, the duration of each of the respiration phases, or the average duration of the respiration cycles or of the respiration phases over defined time intervals during the signal capture, or even the whole respiration signal.

In a further embodiment of the inventive method, the determination of the respiration-dependent heartbeat model comprises dividing the m heartbeat intervals into at least two heartbeat ranges corresponding to the at least two respiration phases. In other words, the ECG signal is divided into at least two heartbeat ranges based upon the respiration phases that have been determined. In this case, the heartbeat intervals which take place within a respiration phase are generally also assigned to this respiration phase. For example, the heartbeat ranges can be assigned 3, 4, 5, 6 or 7 or similar heartbeat intervals. Each heartbeat range need not comprise the same number of heartbeat intervals. The actual number of heartbeat intervals per heartbeat range is patient-specific. In this case, a heartbeat range can always start with the beginning of a heartbeat interval, so that heartbeat ranges and respiration phases can be offset relative to each other.

The division can advantageously also comprise specifying the duration of each heartbeat interval and/or the average duration of the heartbeat intervals of one of the heartbeat ranges over defined time intervals during the signal capture or even over the whole ECG signal. The division can advantageously also comprise specifying the duration of various cardiac phases, e.g. the electrically active and the isoelectrical phase of each heartbeat interval and/or the average duration of these cardiac phases for the heartbeat ranges over defined time intervals during the signal capture or even over the whole ECG signal.

This advantageously comprises the monitoring of the profile of the ECG signal, the identification of extreme points and/or reversal points within the ECG signal, and the assignment in particular of the extrema to specific electrical excitation states of the heart (e.g. QRS complex). For example, an identified signal minimum can be assigned to a Q or S spike, and an identified signal maximum to an R spike within an electrically active cardiac phase. In particular, the isoelectrical cardiac phases of the heartbeat intervals of the exhalation phase are suitable for imaging.

For the purpose of assigning the heartbeat intervals to the heartbeat ranges, an assignment rule can be provided by which heartbeat intervals that include a respiration phase transition are only assigned to one respiration phase in the series of respiration phases. The assignment can take into consideration e.g. the duration of the heartbeat interval concerned and the average duration of the heartbeat intervals in the adjacent heartbeat ranges. Alternatively, the rule can take into consideration whether the respiration phase transition occurs closer to the beginning or the end of the heartbeat interval, and make the assignment on this basis. Alternatively, the heartbeat interval concerned can always be assigned to the heartbeat range which starts or finishes in the heartbeat interval. Depending on the assignment rule, a heartbeat range starts shortly before or shortly after the associated respiration phase.

In an advantageous embodiment of the inventive method, the at least two heartbeat ranges differ in respect of the average duration and/or the average frequency of the assigned heartbeat intervals. The heartbeat intervals which are assigned to the heartbeat range associated with the exhalation phase typically have a longer average duration or a lower frequency in comparison with the heartbeat intervals in the inhalation phase. For example, the duration of the heartbeat intervals in the exhalation phase roughly double in comparison with the heartbeat intervals of the inhalation phase. The average duration of the isoelectrical phase of a heartbeat interval changes accordingly. The precise change between inhalation phase and exhalation phase is patient-specific.

In a further embodiment of the inventive method, both the at least two respiration phases and the at least two heartbeat ranges each occur alternately in the heartbeat model. In other words, each inhalation phase is followed by an exhalation phase and correspondingly the at least two heartbeat ranges occur alternately.

In a further preferred embodiment of the inventive method, each of the at least two heartbeat ranges is assigned a different trigger time-point in accordance with the model. This embodiment advantageously takes into consideration the difference in heartbeat interval duration between the various respiration phases. In other words, consecutive trigger time-points within an inhalation phase are advantageously closer together than in an exhalation phase. The trigger time-points can moreover advantageously take into consideration the duration of the various cardiac phases of a heartbeat interval. It is thus ensured in a particularly precise manner that the image data capture takes place repeatedly at the same point within a heartbeat interval. In particular, the trigger time-points for the isoelectrical phase can be specified based upon an extremum of the electrically active phase.

In a further particularly preferred embodiment of the inventive method, the specification of the at least one trigger time-point comprises specifying a plurality of trigger time-points, each for one heartbeat interval within a heartbeat range. Within a heartbeat range of the patient, the heartbeat intervals are of approximately equal length and therefore, to the extent that this is required for the examination, the heartbeat model can be used to define trigger time-points for multiple (preferably all) heartbeat intervals of the heartbeat range, since the average duration of the heartbeat intervals and the patient-specific duration of cardiac phases are known. In this way, it is possible within a heartbeat range, i.e. within a respiration phase, iteratively to capture reliable image data for the heart in approximately the same state of movement. The examination process can be advantageously accelerated thereby.

The heartbeat range in which a multiplicity of trigger time-points are specified for a plurality of heartbeat intervals is especially preferably the heartbeat range that is assigned to an exhalation phase. As a result of the heartbeat intervals here being distinctly longer than in an inhalation phase, these heartbeat intervals are in principle more suitable for the imaging. Preceding inhalation phases can however be used by a heartbeat model for the purpose of configuring the imaging system, so that the requirements of the specific imaging procedure (which may be dependent on the body region being examined, the patient anatomy, etc.) match the heartbeat model as closely as possible.

If image data must be captured multiple times in the context of the imaging procedure and if the heartbeat intervals of one heartbeat range (typically 4 to 6 heartbeat intervals) are not sufficient, the image data capture can advantageously be continued without interruption by correspondingly establishing further trigger time-points for one or more immediately subsequent heartbeat ranges, taking into consideration the different (average) durations of the heartbeat intervals and/or cardiac phases there. This allows a particularly rapid imaging procedure. Alternatively, the image data capture can omit e.g. an inhalation phase and use two consecutive exhalation phases for the image data capture, wherein the consecutive trigger time-points can also be updated during the course of the examination as described in the introduction.

In a further embodiment of the inventive method, the capture of both the respiration signal and the ECG signal takes place continuously, the heartbeat model is continuously updated during imaging based upon the preceding n respiration cycles and m heartbeat intervals, and the specification of the at least one trigger time-point takes place based upon the updated heartbeat model. In this embodiment, the heartbeat model is advantageously updated continuously during the course of the image data capture process, such that trigger time-points for subsequent image data captures can be predicted as precisely as possible. This approach allows short-term or random irregularities which can occur in addition to the respiratory sinus arrhythmia to be either minimized as a result of averaging or no longer taken into account in the heartbeat model after a certain time. In order to achieve this, provision can be made for a number n of respiration cycles and m heartbeat intervals to be taken into account when calculating the heartbeat model, where the number n and m encompasses the whole period of time for the signal capture or is limited to a number of respiration cycles which is established in advance, e.g. 5, 8, 10, 12, 15 or similar, the number of respiration cycles being completed before the update. In other words, in the second embodiment variant, data relating to older respiration cycles is discarded again. The same applies to the heartbeat intervals assigned to the respiration cycles.

If an embodiment of the inventive method is thus executed multiple times in a sort of repeating loop, it is then possible more accurately to predict the (average) duration for future heartbeat intervals, the position of various cardiac phases, the duration thereof (e.g. based on the model-based average values), etc. and trigger time-points can therefore be defined in an optimal manner.

In a further embodiment, the invention relates to a computing unit for the medical imaging of a patient via a medical imaging system with ECG triggering. In an embodiment, the computing unit is configured to execute at least one embodiment of the inventive method. In an embodiment, the computing unit is therefore designed to capture a respiration signal of the patient comprising n respiration cycles, and concurrently to capture an ECG signal of the patient comprising m heartbeat intervals, to specify a respiration-dependent heartbeat model based upon the n respiration cycles and the m heartbeat intervals, to specify at least one trigger time-point based upon the respiration-dependent heartbeat model, and to start medical imaging via a medical imaging system at the specified trigger time-point.

The computing unit captures and processes the sensor signals, i.e. the respiration signal and the ECG signal, determines the heartbeat model from these, and derives trigger time-points for an image data capture from the heartbeat model. The computing unit then generates corresponding control signals for the imaging system. The computing unit advantageously comprises a plurality of subunits for this purpose.

The computing unit advantageously comprises a subunit in the form of an interface, this being configured to capture or receive the respiration signal and the ECG signal of the patient. The computing unit also comprises a subunit in the form of a specification unit for specifying the heartbeat model and the at least one trigger time-point. In particular, the specification unit is designed to determine respiration phases, heartbeat ranges and cardiac phases, to calculate (average) durations thereof and/or to assign heartbeat intervals to heartbeat ranges, and to use this information alone or in combination when specifying a trigger time-point. The computing unit also comprises a subunit in the form of a control unit. This is designed to generate, based upon the at least one trigger time-point, at least one control signal for the imaging system, in order to start the image data capture. The control signal can be sent to the imaging system via the interface, which can be designed as an input/output interface. The input interface can be designed independently as a separate assembly from the output interface. However, both interfaces can also be integrated in one interface assembly. The further subunits of the computing unit are likewise designed to interact with each other for the purpose of data communication. The interface can serve this purpose also, or separate interfaces can be provided.

The computing unit can preferably be designed as or as part of a computing unit of the medical imaging system. Alternatively, the computing unit can be arranged at a distance or remotely from the medical imaging system, e.g. as part of a central computing and control unit of a medical facility such as a hospital. Data transfers are advantageously effected wirelessly in this case.

In a further embodiment, the invention relates to a system for the medical imaging of a patient via a medical imaging system with ECG triggering. The system comprises:

a capture unit which is designed to capture a respiration signal of the patient comprising n respiration cycles, and concurrently an ECG signal of the patient comprising m heartbeat intervals;

a computing unit which is designed to specify a respiration-dependent heartbeat model based upon the n respiration cycles and the m heartbeat intervals, and a trigger time-point based upon the respiration-dependent heartbeat model; and a medical imaging system which is designed to start medical imaging at the specified trigger time-point.

The capture unit of the system comprises the sensors or measuring device(s) as described in the introduction for the purpose of capturing the respiration signal and the ECG signal of the patient. The computing unit within the system is advantageously integrated in the medical imaging system likewise. Alternatively, the computing unit can also be arranged at a distance or remotely.

A medical imaging system within the meaning of embodiments of the invention most preferably comprises e.g. a computed tomography system or a C-arm x-ray device, in particular comprising a robot stator arm with various axes of adjustment. Other embodiment variants of the medical imaging system are likewise conceivable and lie within the scope of the present invention.

FIG. 1 shows a view of a system S for medical imaging with ECG triggering, comprising a medical imaging system 1 in the form of a computed tomography unit according to an embodiment variant of the present invention. The computed tomography unit 1 shown here has a recording unit 17 for capturing the image data, comprising a radiation source 8 in the form of an x-ray source and, situated opposite this, a radiation detector 9 in the form of an x-ray detector. The x-ray source is an x-ray tube. The x-ray detector is a line scan detector with a plurality of lines. Other medical imaging systems are also possible.

A patient 3 lies on a patient couch 6 or examination table during the image data capture. The patient couch 6 is connected to a couch base 4 in such a way that the latter supports both the patient couch 6 and the patient 3. The patient couch 6 is designed to move the patient 3 along the system axis 5 through the opening 10 of the recording unit 17. The recording unit 17 rotates about the system axis 5 during the image data capture.

The system S comprises a capture unit 26. This is used to capture a respiration signal ATM of the patient 3 comprising n respiration cycles and concurrently an ECG signal EKG of the patient 3 comprising m heartbeat intervals. In this example, the ECG signal EKG can be captured via an example ECG electrode 27 which is arranged on the patient 3. The ECG electrode 27 is designed to capture electrical voltages or potentials of the heart of the patient 3. A plurality of electrodes 27 may be present. The respiration signal ATM is captured here via a chest belt 28, which is likewise arranged on the patient 3. The chest belt 28 is e.g. designed to capture a respiration-related change in length. The capture unit 26 is designed to capture the sensor data of the ECG electrode 27 and the chest belt 28 and to transfer the sensor data to the computing unit 12 of the system S. The capture unit 26 can be designed to perform preprocessing of the sensor data before transfer. In particular, the capture unit 26 is designed to synchronize the sensor data using a clock signal.

The system S further comprises a contrast medium dosing unit 19. A contrast medium in the form of e.g. an iodine solution can be administered to the patient 3 via an injection needle 20 during the image data capture. The flow rate and/or injection time-points for the contrast medium can be controlled by the contrast medium dosing unit 19 as a function of the time in accordance with a defined injection protocol. The contrast medium dosing unit 19 can be designed as an integral part of the x-ray image recording apparatus or arranged in a stationary or mobile manner in the examination room.

The system S also comprises a computing unit 12 in the form of a computer. The computing unit 12 is designed to specify a respiration-dependent heartbeat model HM based upon the n respiration cycles and the m heartbeat intervals, and to specify at least one trigger time-point TP based upon the respiration-dependent heartbeat model HM. The computing unit 12 is connected to the rotatable recording unit 17 for the purpose of data transfer. Control signals for the x-ray image recording are transferred from the computing unit 12 to the recording unit 17 and/or the patient couch 6 via an interface unit 21 and the connection 14. To this end, various scan protocols compatible in each case with a type of examination can be stored in a memory 23 and selected or adapted in advance of an image data capture. The activation of the recording unit 17 and/or the patient couch 6 can take place based upon the specified trigger time-points TP in particular.

In addition to this, image data that has been recorded, e.g. in the form of the at least one projection data record, can be captured by the interface unit 21 for subsequent processing. The computing unit 12 is also connected via the interface unit 21 to the contrast medium dosing unit 19 for the purpose of transferring control signals, in particular for the purpose of synchronizing the dosing of the contrast medium with the image data capture at the specified trigger time-points TP. The computing unit 12 is also designed to capture the respiration signal ATM and the ECG signal EKG via the interface unit 21 and the connection 26. The connections 14, 24, and 25 between the interface unit 21 and the imaging system 1, the contrast medium dosing unit 19 and the capture unit 26 are realized in a known manner, being either wire-based or wireless.

The computing unit 12 comprises a specification unit 22 for specifying the heartbeat model HM and the at least one trigger time-point TZ. The specification unit 22 is designed to perform all of the method steps relating to the heartbeat model HM and the trigger time-points TP. In particular, the specification unit 22 is designed to determine respiration phases, heartbeat ranges, cardiac phases, to calculate (average) durations thereof and/or to assign heartbeat intervals to heartbeat ranges and to use this information alone or in combination when specifying a trigger time-point.

The computing unit 12 also comprises a subunit in the form of a control unit 18. This is designed to generate, based upon the at least one trigger time-point TP, at least one control signal for the imaging system 1, in particular in order to start the image data capture or cause the patient couch to advance. The control unit 18 is further designed to generate, based upon the at least one trigger time-point TP, at least one control signal for the contrast medium dosing unit 19. The control signals can then be sent via the interface unit 21.

The subunits 23, 22 and 18 of the computing unit 12 are likewise designed to interact with each other for the purpose of data communication, e.g. in order to transfer the heartbeat model HM or the calculated trigger time-points TP from the specification unit 22 to the control unit 18. The interface unit 21 can also serve this purpose or separate interfaces can be provided. The interface unit 21 is realized by use of a hardware or software interface such as PCI bus, USB or Firewire. A data transfer is preferably effected via a network connection. The network can be designed as a local area network (LAN), e.g. an intranet, or a wide area network (WAN). According to the invention, the network connection is designed to be wireless, e.g. as a wireless LAN (WLAN or WiFi). The network can comprise a combination of various network examples. Data transfer can take place in response to a data request or autonomously. Data transfer between two units or system components/modules can be bidirectional or unidirectional.

The memory 23, the specification unit 22 and the control unit 18 are embodied here as separate modules which exchange data with each other as necessary. Alternatively, all of the cited units can also be integrated into a single subunit, for example, in respect of either physical or functional integrity.

The computing unit 12 can interact with a computer-readable data medium 13, in particular in order to perform a method according to an embodiment the invention by way of a computer program including program code. Furthermore, the computer program can be retrievably stored on the machine-readable medium. In particular, the machine-readable medium can be a CD, DVD, Blu-Ray Disc, memory stick or hard disk. The memory 23, the specification unit 22 and the control unit 18 can be designed in the form of hardware or software.

For example, the specification unit 22 may be designed as a so-called FPGA (Field Programmable Gate Array) or comprise an arithmetic logic unit. In the example shown here, at least one computer program is stored in the memory 23 of the computing unit 12, wherein the computer program performs all method steps of an embodiment of the inventive method when the computer program is executed on the computer. The computer program comprises program code for executing the method steps of an embodiment of the inventive method.

Furthermore, the computer program can take the form of an executable file and/or be stored on a different computing system than the computing unit 12. For example, the x-ray image recording apparatus can be configured so that the computing unit 12 loads the computer program via an intranet or via the internet into its internal working memory in order to execute the method according to an embodiment of the invention.

Figure 2:
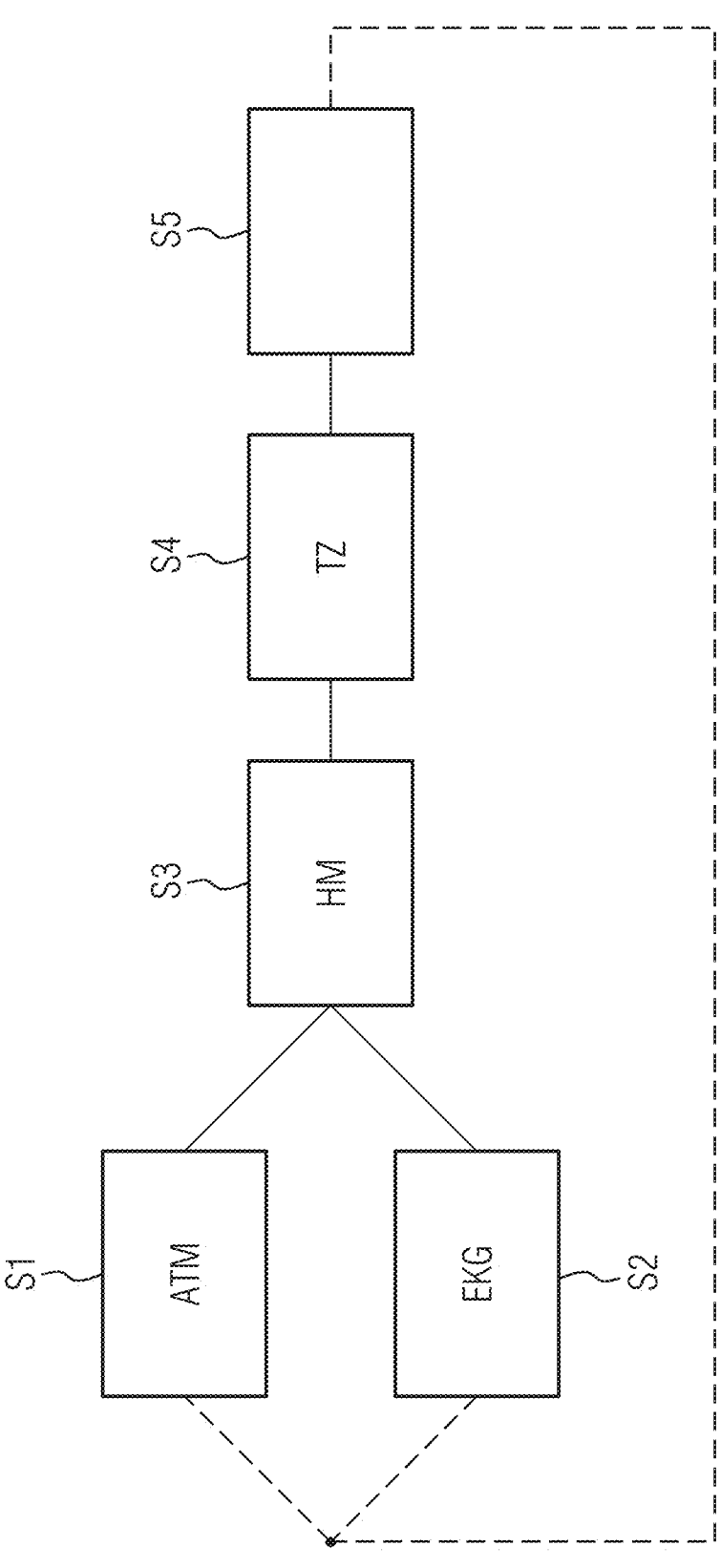
FIG. 2 shows a flow chart of the inventive method according to an example embodiment.

FIG. 2 shows a flow chart of the inventive method according to an example embodiment. The method for the medical imaging of a patient 3 via a medical imaging system 1 with ECG triggering comprises a plurality of steps.

In a first step S1, provision is made for capturing a respiration signal ATM of the patient 3 comprising n respiration cycles. The respiration signal ATM represents the respiration of the patient 3 over various respiration phases AP.

In a second step S2, which takes place concurrently with step S1, provision is made for capturing an ECG signal EKG of the patient 3 comprising m heartbeat intervals. The ECG signal represents the cardiac activity of the patient 3 or the electrical excitation state thereof. The ECG signal covers various cardiac phases HP.

The respiration of the patient 3 influences the duration of cardiac phases HP and therefore the duration of heartbeat intervals HI. This effect is known as respiratory sinus arrhythmia. In order that the influence of the respiration of the patient 3 on the cardiac activity can be ascertained precisely, the temporal relationship between respiration signal and ECG signal must be known. The steps S1 and S2 are executed via a capture unit 26.

In a third step S3, provision is made for determining a respiration-dependent heartbeat model HM which is based on n respiration cycles and m heartbeat intervals of the respiration signal ATM and the ECG signal EKG. Step S3 is executed by the specification unit 22. The heartbeat model HM is used to predict future cardiac activity. In particular, it is used to predict the future profile of the ECG signal EKG, the duration of heartbeat intervals HI and/or the duration of cardiac phases HP while taking the respiration-dependent changes into consideration.

Step S3 in this embodiment comprises dividing the respiration signal ATM, more precisely each respiration cycle AZ, into at least two respiration phases AP.

Figure 3:
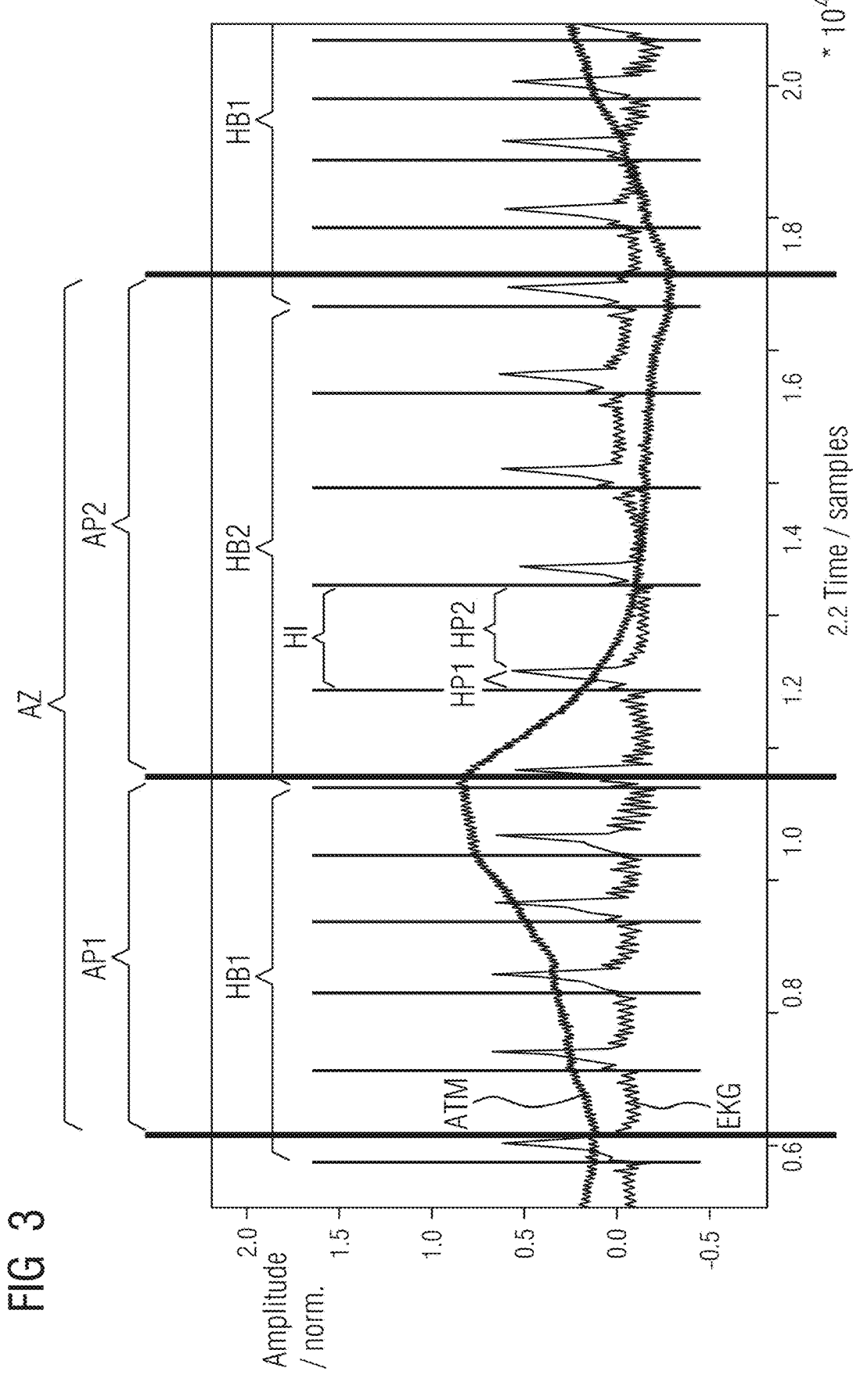
FIG. 3 shows sections of a captured respiration signal and ECG signal.

FIG. 3 shows superimposed sections of respiration signal ATM and ECG signal EKG as captured by the capture unit 26. The illustrated section of the respiration signal ATM comprises n=1 complete respiration cycle AZ.

A respiration cycle AZ of the respiration signal ATM is divided in this example into two respiration phases AP, namely an inhalation phase AP1 and an exhalation phase AP2. An inhalation phase AP1 begins at one of the local minima of the respiration signal ATM. An exhalation phase AP2 begins at one of the local maxima of the respiration signal ATM.

The illustrated section of the ECG signal EKG shows m=14 complete heartbeat intervals HI of the ECG signal EKG. Each heartbeat interval HI in this example comprises two cardiac phases HP, namely an electrically active cardiac phase HP1 and an isoelectrical cardiac phase HP2. The isoelectrical cardiac phase is particularly suitable for medical imaging, since the heart is almost motionless in this phase.

The ECG signal EKG is characterized in that the heartbeat intervals HI are of differing lengths, the length or duration of the heartbeat intervals HI correlating to the respiration phases AP. In the inhalation phase AP1, the heartbeat rate for the patient 3 is approximately 60 beats per minute and the heartbeat intervals HI are correspondingly shorter with a duration of approximately 1000 ms. In the exhalation phase AP2, the heartbeat intervals HI are clearly longer, the heartbeat rate being less than 40 beats per minute here, and the duration of a heartbeat interval HI is more than 1500 ms here.

Based upon their duration or their position in relation to the respiration phases AP, the heartbeat intervals HI can be assigned to one of two different heartbeat ranges HB here.

Accordingly, step S3 in this embodiment comprises dividing the m heartbeat intervals HI into two heartbeat ranges HB corresponding to the at least two respiration phases AP. Accordingly, the two heartbeat ranges HB differ in respect of the average duration and/or the average frequency of the assigned heartbeat intervals HI. Heartbeat range HB1 is assigned to the inhalation phase AP1 in this case. Heartbeat range HB2 is assigned to the exhalation phase AP2 in this case. In this embodiment each of the heartbeat ranges HB comprises five heartbeat intervals, which can be taken into consideration for the purpose of determining the average duration/frequency per heartbeat range HB. Averaging over a plurality of successive heartbeat ranges HB1 or HB2 can however also take place in order to eliminate statistical fluctuations as far as possible.

Heartbeat intervals which include a respiration phase transition (an extreme point of the respiration signal ATM) are assigned to the earlier heartbeat range HB if the extreme point occurs closer to end of the heartbeat range HB, or to the later heartbeat range HB if the extreme point occurs closer to the beginning of the heartbeat range HB. Alternative assignment rules are also possible and can be stored e.g. in the memory 23 for retrieval by the specification unit.

Figure 4:
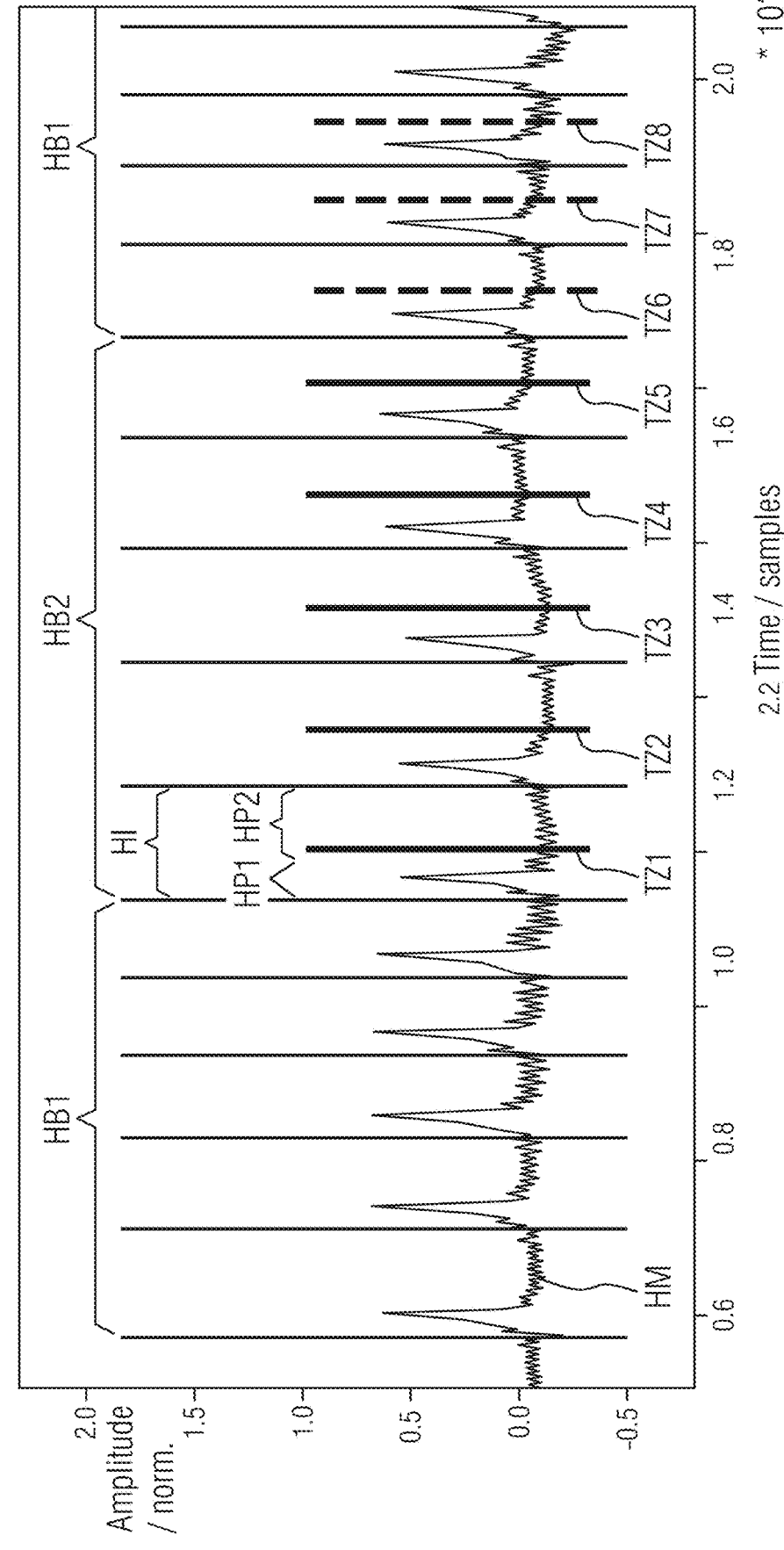
FIG. 4 shows a section of a specified respiration-dependent heartbeat model HM in an example embodiment of the invention.

FIG. 4 shows a section of a specified heartbeat model HM in an example embodiment of the invention. In a similar manner to the two respiration phases AP1 and AP2, the two heartbeat ranges HB1 and HB2 also occur alternately in the heartbeat model HB. The heartbeat model HM can use the average duration of the heartbeat intervals HI for the two heartbeat ranges HB1 and HB2 for future cardiac activity. Alternatively, the heartbeat model HM can perform a weighted averaging when specifying the average duration of the heartbeat intervals HI of one of the heartbeat ranges HB, in order to emphasize representative/frequent heartbeat intervals and achieve a more accurate prediction for the heartbeat ranges HB.

In a fourth step S4, provision is made for specifying at least one trigger time-point TZ based upon the respiration-dependent heartbeat model HM. Step S4 is likewise executed by the specification unit 22.

Provision is preferably made for specifying not only one trigger time-point TZ, but a plurality of trigger time-points TZ, each for one heartbeat interval HI. Depending on the type of medical examination to be performed on the patient 3, trigger time-points TZ are determined for successive heartbeat intervals, wherein both heartbeat ranges HB1 and HB2 are taken into consideration. Alternatively, if an examination requires longer capture times, it is possible to specify trigger time-points TZ for only a plurality of or all heartbeat intervals HI of consecutive heartbeat ranges HB2 corresponding to exhalation phases AP2. The choice of suitable heartbeat intervals HI for imaging depends on the type of examination, the constitution of the patient, the examination time available, the number of heartbeat intervals HI per heartbeat range HB, or similar, and is established by the specification unit 22. By virtue of the predetermined examination type, the corresponding imaging protocol with a plurality of protocol parameters, and the heartbeat model HM with its patient-specific heartbeat ranges HB and the average duration of the heartbeat intervals HI which varies in a respiration-related manner between the heartbeat ranges HB, it is now possible to define ideal trigger time-points TZ at which an image data capture should take place. In the present embodiment, the specification unit 22 assigns each of the at least two heartbeat ranges HB1 and HB2 a different trigger time-point in accordance with the model, wherein the trigger time-point here relates to the temporal separation of the trigger from a beginning of a heartbeat interval HI or a beginning of a cardiac phase, e.g. the isoelectrical phase HP2. This separation differs between the heartbeat ranges HB1 and HB2.

A plurality of trigger time-points TZ are specified in this embodiment, each for one heartbeat interval HI within a heartbeat range HB. In this case, the heartbeat range is in particular the heartbeat range HB2, which is assigned to an exhalation phase AP2. By way of example, FIG. 4 shows five trigger time-points TZ1, TZ2, TZ3, TZ4 and TZ5 for the heartbeat intervals HI of the heartbeat range HB2. These are so disposed as to be temporally equidistant from each other and all have the same separation from the beginning of the respective heartbeat interval HI.

By way of example, FIG. 4 shows three further and in particular optional (hence broken marked) trigger time-points TZ6, TZ7 and TZ8 for the heartbeat intervals HI of the heartbeat range HB1. These may be required if in the context of an examination image data has to be captured multiple times and one heartbeat range is not sufficient for this. The trigger time-points TZ6, TZ7 and TZ8 are likewise temporally equidistant from each other and all have the same separation from the beginning of the respective heartbeat interval HI. However, in accordance with the shortened average duration of the heartbeat intervals HI in the heartbeat range HB1, both separations are smaller in comparison with the separations of the trigger time-points TZ1, TZ2, TZ3, TZ4 and TZ5.

In a fifth step S5, provision is made for starting the medical imaging at the specified trigger time-point or timepoints TZ. Step S5 is executed via the control unit 18, which generates and sends corresponding control signals to the recording unit 17 of the imaging system 1. In step S5, the recording unit 17 and/or the patient couch 6 and/or the contrast medium dosing unit 19 and/or a further component of the system S can be preconfigured in accordance with the respiration-dependent heartbeat model. This preconfiguration comprises, in addition to generating the actual start control signals at the control time-points that have been determined, generating further control signals which preconfigure the medical imaging system and/or further units, thereby adapting these to the respiration-dependent heartbeat model. The preconfiguration can comprise the setting of an initial position for the patient couch, from which the image data capture is started at the trigger time-point. The preconfiguration can comprise the setting of bolus sizes and/or contrast medium flow rates. The preconfiguration can also comprise the setting of an x-ray tube voltage. Accordingly, the control unit 18 also generates control signals for the patient couch 6 in order to move the patient couch 6 to a position that is required for the image data capture. The control unit 18 optionally also generates control signals for a contrast medium dosing unit 19 based upon the specified trigger time-points TZ. The specification of multiple trigger time-points TZ for heartbeat intervals HI of one or more heartbeat ranges HB therefore allows optimal (pre) configuration of the image data capture. For example, the image data capture can already be started in a shorter heartbeat range HB1 by starting the patient couch movement or the contrast medium injection or similar, so that all heartbeat intervals HI of the heartbeat range HB2 can be utilized for the imaging.

Provision can optionally be made for performing steps S1 to S5 continuously or repeatedly. Accordingly, the capture of both the respiration signal and the ECG signal can take place continuously. The heartbeat model can be continuously updated during imaging based upon the preceding n respiration cycles and m heartbeat intervals, and the specification of a trigger time-point takes place based upon the updated heartbeat model. This is indicated in FIG. 2 by the broken line.

Where not explicitly developed but applicable and for the purposes of the invention, individual example embodiments and individual part-aspects or features of the example embodiments may be combined with each other or substituted without thereby departing from the scope of the present invention. Advantages of the invention that are described with reference to one example embodiment also apply where transferable to other example embodiments without this being explicitly stated.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for medical imaging of a patient using a medical imaging system with ECG triggering, the method comprising:

capturing a respiration signal of the patient, the respiration signal including n respiration cycles;

concurrently capturing an ECG signal of the patient, the ECG signal including m heartbeat intervals;

determining a respiration-dependent heartbeat model based upon the n respiration cycles and the m heartbeat intervals by dividing the respiration signal into at least two respiration phases and dividing the m heartbeat intervals into at least two heartbeat ranges, each of the at least two heartbeat ranges corresponding to a respiration phase of the at least two respiration phases;

specifying at least one trigger time-point based upon the respiration-dependent heartbeat model; and starting the medical imaging at the at least one trigger time-point specified;

wherein the respiration-dependent heartbeat model is initially determined while the patient is at rest, such that the at least two respiration phases include an inhalation phase and an exhalation phase; and wherein the respiration-dependent heartbeat model includes modifications to a breathing pattern of the patient as additional phases of the at least two respiration phases.

2. The method of claim 1, wherein the starting of the medical imaging includes preconfiguring the medical imaging system in accordance with the respiration-dependent heartbeat model.

3. The method of claim 1, wherein the at least two heartbeat ranges differ in respect of at least one of average duration and average frequency of assigned heartbeat intervals.

4. The method of claim 1, wherein each of the at least two respiration phases and each of the at least two heartbeat ranges occur alternately in the respiration-dependent heartbeat model.

5. The method of claim 1, wherein each of the at least two heartbeat ranges is assigned a respectively different trigger time-point according to the respiration-dependent heartbeat model.

6. The method of claim 1, wherein the specifying of the at least one trigger time-point includes specifying a plurality of trigger time-points, each respective one of the plurality of trigger time-points being specified for one respective heartbeat interval within a heartbeat range.

7. The method of claim 6, wherein the heartbeat range is assigned to the exhalation phase.

8. The method of claim 1, wherein the capturing of the respiration signal and the ECG signal takes place continuously;

the respiration-dependent heartbeat model is continuously updated to continuously produce an updated heartbeat model during imaging based upon the n respiration cycles and the m heartbeat intervals; and the specifying of a trigger time-point is based upon the updated heartbeat model.

9. A computing unit for medical imaging of a patient using a medical imaging system with ECG triggering, the computing unit being designed to capture a respiration signal of the patient, the respiration signal including n respiration cycles;

concurrently capture an ECG signal of the patient, the ECG signal including m heartbeat intervals;

determine a respiration-dependent heartbeat model based upon the n respiration cycles and the m heartbeat intervals by dividing the respiration signal into at least two respiration phases and dividing the m heartbeat intervals into at least two heartbeat ranges, each of the at least two heartbeat ranges corresponding to a respiration phase of the at least two respiration phases;

specify at least one trigger time-point based upon the respiration-dependent heartbeat model; and start the medical imaging at the at least one trigger time-point specified;

wherein the respiration-dependent heartbeat model is initially determined while the patient is at rest, such that the at least two respiration phases include an inhalation phase and an exhalation phase; and wherein the respiration-dependent heartbeat model includes modifications to a breathing pattern of the patient as additional phases of the at least two respiration phases.

10. A system for medical imaging of a patient via ECG triggering, comprising:

a capture unit designed to capture a respiration signal of the patient, the respiration signal including n respiration cycles, and concurrently capture an ECG signal of the patient, the ECG signal including m heartbeat intervals;

a computing unit designed to specify a respiration-dependent heartbeat model based upon the n respiration cycles and the m heartbeat intervals by dividing the respiration signal into at least two respiration phases and dividing the m heartbeat intervals into at least two heartbeat ranges, each of the at least two heartbeat ranges corresponding to a respiration phase of the at least two respiration phases, and at least one trigger time-point based upon the respiration-dependent heartbeat model;

wherein the respiration-dependent heartbeat model is initially determined while the patient is at rest, such that the at least two respiration phases include an inhalation phase and an exhalation phase; and wherein the respiration-dependent heartbeat model includes modifications to a breathing pattern of the patient as additional phases of the at least two respiration phases; and a medical imaging system designed to start the medical imaging at the at least one trigger time-point.

11. The method of claim 3, wherein each of the at least two respiration phases and each of the at least two heartbeat ranges occur alternately in the respiration-dependent heartbeat model.

12. The method of claim 3, wherein each of the at least two heartbeat ranges is assigned a respectively different trigger time-point according to the respiration-dependent heartbeat model.

13. The method of claim 2, wherein the specifying of the at least one trigger time-point includes specifying a plurality of trigger time-points, each respective one of the plurality of trigger time-points being specified for one respective heartbeat interval within a heartbeat range.

14. The method of claim 13, wherein the heartbeat range is assigned to the exhalation phase.

15. The method of claim 2, wherein the capturing of the respiration signal and the ECG signal takes place continuously;

the respiration-dependent heartbeat model is continuously updated to continuously produce an updated heartbeat model during imaging based upon the n respiration cycles and the m heartbeat intervals; and the specifying of a trigger time-point is based upon the updated heartbeat model.

16. A non-transitory computer readable medium storing computer code which, when run on at least one processor, configures the at least one processor to perform the method of claim 1.

17. A non-transitory computer readable medium storing computer code which, when run on at least one processor, configures the at least one processor to perform the method of claim 2.

\* \* \* \* \*